United States Patent
Schulat et al.

(10) Patent No.: US 7,477,404 B2
(45) Date of Patent: Jan. 13, 2009

(54) METHOD FOR ANALYZING A SAMPLE ON A TEST ELEMENT AND ANALYSIS SYSTEM FOR SAME

(75) Inventors: Jochen Schulat, Mannheim (DE); Bernd Stenkamp, Heidelberg (DE); Guenter Schmelzeisen-Redeker, Losrsch (DE); Wilfried Schmid, Mannheim (DE); Dieter Meinecke, Mannheim (DE); Kai Dickopf, Bad Rappenau (DE); Gertrud Albrecht, Mannheim (DE); Andreas Menke, Mannheim (DE); Bernhard Kern, Heidelberg (DE); Wolfgang Schwoebel, Mannheim (DE); Stefan Kalveram, Veirnheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 11/848,779

(22) Filed: Aug. 31, 2007

(65) Prior Publication Data

US 2008/0106730 A1 May 8, 2008

(30) Foreign Application Priority Data

Nov. 7, 2006 (EP) .................... 06123573

(51) Int. Cl.
G01B 11/14 (2006.01)
G01N 33/48 (2006.01)
(52) U.S. Cl. ........................ 356/614; 356/39
(58) Field of Classification Search .............. 356/614, 356/39
See application file for complete search history.

(56) References Cited

U.S. PATENT DOCUMENTS 5,424,035 A * 6/1995 Hones et al. .................. 422/55

(Continued)

FOREIGN PATENT DOCUMENTS

CA 2311496 A1 6/1999

(Continued)

Primary Examiner—Roy M Punnoose
(74) Attorney, Agent, or Firm—Justin L. Sage; Roche Diagnostics Operations, Inc.

(57) ABSTRACT

The invention relates to embodiments of a method and a system for monitoring the correct positioning of a test element in a test element receptacle of an analysis unit, the test element carrying a sample to be analyzed by the analysis unit. Using a delimiting element, responsive signals resulting from irradiating an analysis region on the test element are effectively prevented from impinging upon a signal detector when the analysis region is in an incorrect position relative to the analysis unit. The delimiting element is provided with a light-opaque region and a light-transmissive region, and the light-opaque region is positioned such that responsive signals impinge upon it rather than the light-transmissive region when the analysis region is in an incorrect position. The embodiments of the invention further relate to methods and systems configured to further analyze the sample, to determine whether the sample has been underdosed, and additional position monitoring steps comprising irradiating different partial regions of the analysis region and comparing the detection signals responsive to each to a predetermined limit value.

12 Claims, 4 Drawing Sheets

U.S. PATENT DOCUMENTS

| | | | |
|---|---|---|---|
| 5,597,532 A * | 1/1997 | Connolly | 422/58 |
| 5,801,817 A * | 9/1998 | Riedel | 356/4.07 |
| 5,846,837 A | 12/1998 | Thym et al. | |
| 6,036,919 A | 3/2000 | Thym et al. | |
| 6,055,060 A * | 4/2000 | Bolduan et al. | 356/433 |
| 6,458,596 B1 | 10/2002 | Poellmann | |
| 6,707,554 B1 | 3/2004 | Miltner et al. | |
| 6,906,802 B2 * | 6/2005 | Voelkel | 356/446 |
| 7,008,799 B1 | 3/2006 | Zimmer et al. | |
| 2002/0132363 A1 | 9/2002 | Rehm | |
| 2007/0171398 A1 * | 7/2007 | Petrich | 356/39 |

FOREIGN PATENT DOCUMENTS

| | | |
|---|---|---|
| DE | 19753847 A1 | 6/1999 |
| DE | 19932846 A1 | 1/2001 |
| EP | 0618443 B1 | 5/1994 |
| EP | 0819943 A2 | 1/1998 |
| EP | 0821233 B1 | 1/1998 |
| EP | 0821234 B1 | 1/1998 |
| EP | 1213579 B1 | 6/2002 |
| WO | 97/02487 A1 | 1/1997 |
| WO | 00/19185 A1 | 4/2000 |

* cited by examiner

METHOD FOR ANALYZING A SAMPLE ON A TEST ELEMENT AND ANALYSIS SYSTEM FOR SAME

REFERENCE TO RELATED APPLICATIONS

The present application is based on and claims priority to European Patent Application No. 06123573.5, filed Nov. 7, 2006, which is hereby incorporated by reference in its entirety.

BACKGROUND

The invention relates to a method for analyzing a sample on a test element in an analysis system, in particular for measuring, the concentration of glucose in a body fluid on a test strip.

In order to analyze samples, for example body fluids such as blood or urine, it is common to use analysis systems in which samples to be analyzed are situated on a test element and react in a test field if appropriate with one or more reagents on the test element before they are analyzed. The optical, in particular photometric, and electrochemical evaluation of test elements are the most commonly used methods for rapidly determining the concentration of analytes in samples. Analysis systems with test elements for sample analysis are generally used in the field of analysis, environmental analysis and primarily in the field of medical diagnosis. Test elements which are evaluated photometrically or electrochemically are of great value, particularly in the field of blood glucose diagnosis from capillary blood.

There are various forms of test elements. For example small substantially square sheets, also referred to as slides, in the middle of which there is a multilayer test field are known. Diagnostic test elements which are in the form of strips are referred to as test strips. Test elements are comprehensively described in the prior art, for example in the documents DE-A 197 53 847, EP-A 0 821 233, EP-A 0 821 234 or WO 97/02487. The present invention relates to test elements of any desired form, including strip-type, test elements.

Test elements in which a sample is applied to a sample application site and is transported by means of capillary force into an analysis region (test field) separate from the sample application site are known in the prior art. Such a test element is the subject matter of DE 197 53 847 A1, for example.

For the analytical investigation of a sample on a test element, test element analysis systems containing a test element receptacle or mount for positioning the test element in a measurement or analysis position and a measurement and evaluation device, also referred to as an analysis unit, for carrying out a measurement and determining an analysis result based on this are known in the prior art.

In order to mount the test element in the analysis position, known positioning devices have a displaceably mounted pin with an end that tapers conically towards the bottom. When suitably positioned, the tip of the pin is situated in a recess provided in the test element, with the result that the test element is fixed and positioned in the direction of its longitudinal axis. The pin can also serve to electrically signal the presence of a test element or the positioning thereof. For this purpose, the pin is embodied in electrically conductive fashion and a contact is provided e.g. on the opposite side of the apparatus to said pin. When there is no test element, the pin is pressed against the contact by means of a spring and an electrical contact is made between these two elements. If a test element is then inserted, it initially pushes itself between the pin and the contact, with the result that the electrical contact is cancelled. However, as the test element is pushed further, the pin engages through the groove in the test element and the electrical contact is closed again. The contact can e.g. also be actuated by a lateral cantilever of the pin.

In many known analysis systems, the positioning of a test element relative to an analysis unit is critical, particularly in the case of an optical evaluation of test elements. A relative positioning of the analysis region of a test element with respect to the evaluation optical system is of crucial importance for the precision and correctness of the measurement carried out for the analysis of a sample in the analysis region.

Many solutions are provided in the prior art for ensuring a correct positioning. In the above example of a positioning device, correct positioning of the test element in the longitudinal direct (X direction) is ensured as a result of the pin engaging into the recess in the test element. For positioning in the transverse direction (Y direction), the positioning device may comprise guide elements. In this and also in many other positioning devices for test elements in analysis systems, however, an incorrect positioning in a perpendicular direction with respect to the analysis region (Z direction) cannot be precluded. By way of example, a user can raise the test element at the side remote from the pin in such a way that the positioning of the analysis region relative to the analysis unit of the analysis system changes in such a way that the analysis result is corrupted. Even in the case of a mounting at both ends of a strip-type test element, for example by means of a pin engaging into a recess at one end and a holding-down device, bearing on the test element surface, at the other end of the test element, an incorrect position of the analysis region in the Z direction can occur it the test element has flexed between the two holding elements. Therefore, an analysis system for analyzing a sample on a test element must be able to identify such an incorrect positioning in the Z direction in order to avoid the indication of erroneous analysis results by the analysis system.

The object of the present invention is to provide a method for analyzing a sample on a test element in an analysis system, and an analysis system for analyzing a sample on an analytical test element which avoid the disadvantages of the prior art. In particular, in the case of the method according to the invention and the analysis system according to the invention, the object is to identify an incorrect positioning of the analysis region of a test element in the Z direction. Furthermore, the method according to the invention and the analysis system according to the invention are intended to react more sensitively to an incorrect positioning in the Z direction, particularly in the case of flexure of the test element in the Z direction in a test element receptacle of an analysis system.

SUMMARY OF THE EMBODIMENTS OF THE INVENTION

These objects and more are achieved according to the present invention disclosed herein by means of a method for analyzing a sample on a test element in an analysis system, and an analysis system for conducting such method. The analysis system generally comprises a test element receptacle, an analysis unit adapted to carry out the embodiments of the methods disclosed herein, and various other structural elements configured for use of the embodiments of the system and for carrying out the embodiments of the method.

In one embodiment, the present invention comprises a method for monitoring whether an analysis region of the test element is correctly positioned in the test element receptacle in an analysis position relative to the analysis unit, comprising the steps of irradiating the analysis region with light from at least one monitoring light source; detecting responsive detection signals by a detector, the detection signals comprising light scattered and/or reflected at the analysis region, the detector signals configured to detect such detection signals; delimiting a light-transmissive region arranged between the test element and the detector by a delimiting element comprising a light-opaque region and positioned relative to the monitoring light-source and the detector such that detection signals generally impinge upon the light-opaque region and not the detector when the test element is mounted in the test element receptacle in an incorrect position in a Z direction; evaluating the detection signals detected by the detector using an evaluation unit; and comparing the detected detection signals with at least one predetermined limit value corresponding to a correct analysis position with respect to the Z direction.

In other embodiments, the present invention relates to an analysis system for analyzing a sample on an analytical test element, the system having an analysis unit, and a test element to be analyzed being positioned in a test element receptacle relative to the analysis unit. The analysis system has a monitoring unit for monitoring whether an analysis region of the test element is positioned in the test element receptacle in an analysis position relative to the analysis unit, the monitoring unit comprising at least one monitoring light source for irradiating the analysis region with light, a detector for detecting monitoring detection signals comprising light scattered and/or reflected at the analysis region, and an evaluation unit. A delimiting element is arranged between a test element arranged in the test element receptacle and the detector, said delimiting element having a light-opaque region. The delimiting element is positioned relative to the monitoring light source and the detector in such a way that the monitoring detection signals of a test element that is arranged in the test element receptacle in an incorrect position in the Z direction generally impinges on the light-opaque region and not the detector. The evaluation unit compares the monitoring detection signals with at least one predetermined limit value and is configured to identify an incorrect position of the analysis region in the Z direction in the case where the limit value is undershot. The analysis system according to the invention can be used in particular for carrying out the method according to the invention.

In yet other embodiments of the present invention, an analysis of a sample on a test element positioned in the test element receptacle in the analysis position is carried out once the monitoring of the correct position of the test element determines that the test element is in the analysis position. In typical embodiments, analyzing the sample comprises the steps of irradiating the analysis region with light from at least one analysis light source; using a detector, detecting analysis signals comprising light scattered and/or reflected at the analysis region; and evaluating the analysis signals by the evaluation unit for obtaining analysis results.

Analyzing methods in other embodiments may further comprise irradiating first and second zones of analysis region using first and second analysis light sources, detecting first and second analysis signals and comparing the signals using the evaluation unit in order to select one of the first or second analysis signals for purposes of determining an analyte concentration contained in the sample.

In yet other embodiments of the present invention, steps are included for detecting underdosing of sample in the analysis region one sample has been applied to the sample application location of the test element. Exemplary steps for detecting underdosing of sample include the steps of applying a sample to the sample application location of the test element; activating at least one analysis light source for irradiating a first partial region of the analysis region and, using a detector, detecting first detection signals comprising the analysis light scattered and/or reflected by the first partial region; activating a monitoring light source for irradiating a second partial region of the analysis region, the second partial region typically being further away from the sample application location than the first partial region, and, using a detector, detecting second detection signals comprising the monitoring light scattered and/or reflected by the second partial region; calculating a difference value by subtracting the second detection signal from the first detection signal, and comparing the difference value with a predetermined first difference value by the evaluation unit for identifying an underdosing of the sample in the case where the predetermined first difference value is exceeded.

In yet other embodiments of the present invention, the method for monitoring the correct positioning of a test element in the analysis region in the Z direction can include additional steps for ensuring the accuracy of such monitoring. Exemplary embodiments of a more accurate monitoring method comprise the steps of applying a sample to a sample application location of the test element; activating at least one analysis light source for irradiating a first partial region of the analysis region and, using a detector, detecting first detection signals comprising the analysis light scattered and/or reflected by the first partial region; activating a monitoring light source for irradiating a second partial region of the analysis region, the second partial region typically being further away from the sample application location than the first partial region, and, using a detector, detecting second detection signals comprising the monitoring light scattered and/or reflected by the second partial region; calculating a difference value by subtracting the first detection signals from the second detection signals, and comparing the difference value with a predetermined second difference value for identifying an incorrect position of the analysis region in the Z direction in the test element receptacle.

BRIEF DESCRIPTION OF THE DRAWINGS

The following detailed description of the embodiments of the present invention can be best understood when read in conjunction with the following drawings, where like structure is indicated with like reference numerals and in which.

Figure 1:
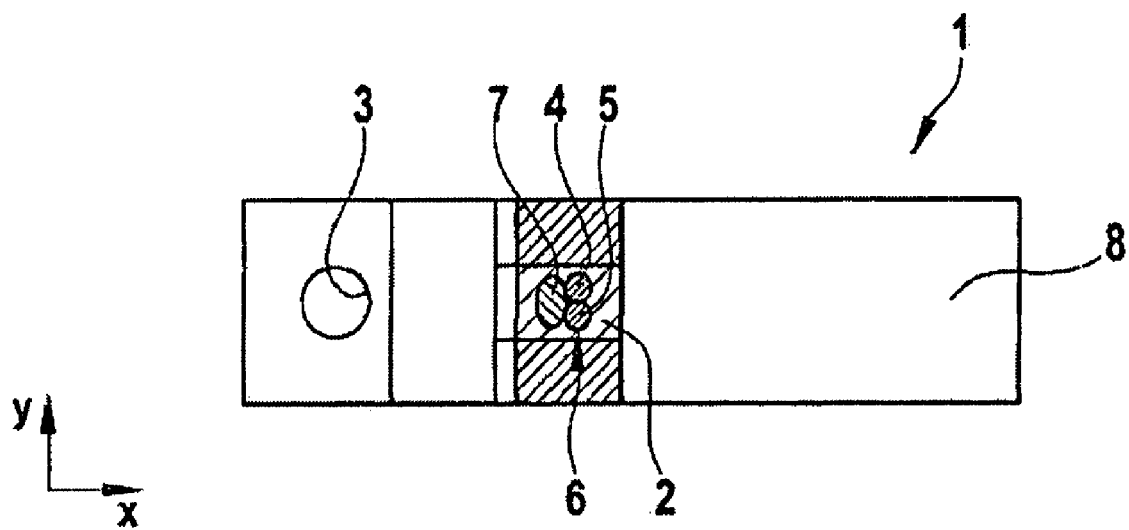
FIG. 1 illustrates a top view of a test element for use in the method or with the analysis system, according to embodiments of the present invention.

Skilled artisans appreciate that elements in the figures are illustrated for simplicity and clarity and have not necessarily been drawn to scale. For example, the dimensions of some of the elements in the figure may be exaggerated relative to other elements to help improve understanding of the embodiment(s) of the present invention.

In order that the present invention may be more readily understood, reference is made to the following examples, which are intended to illustrate the present invention, but not limit the scope thereof.

DETAILED DESCRIPTION OF EMBODIMENTS OF THE PRESENT INVENTION

The following description of the preferred embodiment is merely exemplary in nature and is in no way intended to limit the present invention or its application or uses.

In embodiments of methods for monitoring the correct positioning of a test element in an analysis position in the test element receptacle, a light-transmissive region can be arranged between the test element, and the detector is delimited by a delimiting element having a light-opaque region, the delimiting element being positioned relative to a light source and the detector in such a way that responsive signals, comprising the irradiating light scattered and/or reflected at the analysis region, from a test element that is arranged in the test element receptacle in an incorrect position in the Z direction generally impinges on the light-opaque region and not the detector. The responsive detection signals obtained by the detector are compared with a predetermined limit value, such that an incorrect position in the Z direction is identified in the event that the limit value is undershot.

In certain embodiments, the test element receptacle of the analysis system is that part which receives the test element during an analysis of a sample on the test element and mounts the test element. In further embodiments, the analysis unit is a component part of the analysis system which serves for the analysis of a test element in the test element receptacle, such as an optically measuring arrangement which effects the analysis by irradiating an analysis region of the test element and detecting and evaluating scattered, reflected or transmitted radiation.

The method according to the invention is carried out with a test element that is provided for the analysis of a sample and is arranged in the test element receptacle. For this purpose, the test element may have been positioned manually or automatically in the test element receptacle relative to the analysis unit. According to embodiments of the invention, a monitoring is carried out to ascertain whether the analysis region of the test element is positioned in the test element receptacle in an analysis position relative to the analysis unit. In this case, the analysis position is that position of the test element in the test element receptacle which is configured to carry out an analysis of a sample in the analysis region of the test element. It is, therefore, that position of the test element in the test element receptacle at which there is no incorrect positioning of the analysis region in the Z direction, in particular no incorrect positioning of the analysis region in the X, Y and Z directions, relative to the analysis unit.

According to embodiments of the present invention, the analysis region is that region of the test element in which the sample is analyzed. Typically, said region contains a reagent system that reacts with an analyte contained in the sample and thereby brings about detectable changes. For the analysis, the sample is brought into contact with the analysis region, the sample being transported for example from a sample application location towards the analysis region by means of a capillary gap.

According to the embodiments of the present invention, monitoring whether the analysis region of the test element is positioned in the test element receptacle in the analysis position relative to the analysis unit comprises the steps of irradiating the analysis region with light from at least one monitoring light source; using a detector, detecting responsive detection signals from light scattered and/or reflected at the analysis region; and evaluating the detection signals by an evaluation unit.

Suitable light sources according to embodiments of the present invention include light sources having a substantially continuous emission spectrum, such as incandescent lamps for example, and also those having a so-called band spectrum, such as light-emitting diodes for example. Light-emitting diodes are suitable for use in a portable analysis system because they have a relatively high efficiency, which is helpful for battery-operated instruments. Furthermore, light-emitting diodes are obtainable for a series of wavelength ranges in the visible region and also in the infrared region. Typically, embodiments of the present invention use a light source which emits the principal part of its radiation in a wavelength range that is greatly absorbed by the analysis region after it has reacted with analyte. By way of example, laser diodes can be used as light sources. In other embodiments of the present invention, the light sources can be activated successively, there typically being certain embodiments in which there is a time period of less than about 0.5 seconds between the times at which the light sources are activated.

Semiconductor components known in the prior art, such as photodiodes, phototransistors or photovoltaic elements, may suitably be used as detectors in embodiments of the present invention.

In other embodiments of the present invention, a delimiting element delimits a light-transmissive region through which the responsive signals, comprising the irradiating light that is scattered and/or reflected at the analysis region, can pass to the detector. Typically, the delimiting element is positioned relative to the light source and the detector in such a way that, in the event of an incorrect positioning of the analysis region in the Z direction, the light from the light source that is scattered and/or reflected at the analysis region of the test element generally impinges on the light-opaque region of the delimiting element. As a result, a predominant portion of the responsive detection signal is blocked by the light-opaque region in such a way that it generally does not impinge on the detector. Therefore, in the case of an incorrect positioning in the Z direction, the detection signals of the detector lie below a defined limit value. By comparing the detection signals with at least one predetermined limit value, the incorrect position of the analysis region in the Z direction can therefore be identified in the case where the limit value is undershot.

According to embodiments of the invention, light signals that are responsive to the light irradiating the analysis region comprise the responsive detection, monitoring and/or analysis signals of the irradiating light scattered and/or reflected at the analysis region, depending on the purpose for which the light is irradiating the analysis region (as described herein). The signals are detected by a detector adapted for obtaining such signals. In connection with the embodiments of the present invention, scattered and/or reflected light typically relates to scattered and/or diffusely reflected light, as well as scattered, diffusely reflected or regularly reflected light. Generally speaking, light reflection is the flowing back of the light when it impinges on the interface between two media. Also generally speaking, light scattering is light deflection caused by small particles as it passes through a medium. In the case of diffuse reflection, the light that is incident (typically in directional fashion) is radiated back in a manner scattered in many directions. The law of reflection holds true for regular (regular, directional, specular) reflection. Typically, in embodiments of the method according to the present invention, the detector detects one of (1) the light scattered at the analysis region, (2) the light diffusely reflected at the analysis region, or (3) the light scattered at the analysis region and the light diffusely reflected at the analysis region, for monitoring whether the analysis region is positioned in the analysis position.

In exemplary embodiments of the present invention, the light-opaque framing of an optical window present in an optical analysis system may serve as the delimiting element.

The method according to embodiments of the present invention is used in analysis systems in which an incorrect positioning of the analysis region of a test element leads to a corruption of analysis results. In particular, these are optically measuring systems for the photometric analysis of a sample. The method according to the invention is preferably used in relatively small analysis systems which can be operated by a patient himself/herself. Such a system is described for example in EP-B 0 618 443, which is hereby incorporated by reference herein. The invention is of particular importance for those systems in which test elements are used which can be bent along their longitudinal axis and which are mounted only at one end or at both sides or ends by the analysis instrument, for example by means of a pin engaging into a recess and, if appropriate, a holding-down device bearing on the test element surface.

In the present invention, the use of a delimiting element advantageously results in a significant reduction of the intensity of responsive signals from a test element that is incorrectly positioned in the Z direction, such that the incorrect positioning can be identified with high reliability on the basis of the detection signals obtained. Responsive signals typically comprise the light scattered and/or reflected at the analysis region from a light irradiating the analysis region from a light source.

The invention furthermore relates to an analysis system for analyzing a sample on an analytical test element, the system having an analysis unit, a test element to be analyzed being positioned in a test element receptacle relative to the analysis unit. The analysis system has a monitoring unit for monitoring whether an analysis region of the test element is positioned in the test element receptacle in an analysis position relative to the analysis unit, the monitoring unit comprising at least one monitoring light source for irradiating the analysis region with light, a detector for detecting monitoring detection signals comprising light scattered and/or reflected at the analysis region, and an evaluation unit. A delimiting element is arranged between a test element arranged in the test element receptacle and the detector, said delimiting element having a light-opaque region. The delimiting element is positioned relative to the monitoring light source and the detector in such a way that the monitoring detection signals of a test element that is arranged in the test element receptacle in an incorrect position in the Z direction generally impinges on the light-opaque region and not the detector. The evaluation unit compares the monitoring detection signals with at least one predetermined limit value and is configured to identify an incorrect position of the analysis region in the Z direction in the case where the limit value is undershot. The analysis system according to the invention can be used in particular for carrying out the method according to the invention.

In one embodiment, the monitoring unit may correspond to the analysis unit of the analysis system such that the at least one monitoring light source and the detector are used both for the position monitoring of the analysis region and for the analysis of a sample in the analysis region. However, in other embodiments separate monitoring and analysis units may also be present in the analysis system according to the invention.

In accordance with one embodiment of the present invention, for the detection signals in the case of an incorrect positioning of the analysis region of the test element in the Z direction, a limit value for the relative reflectance is predetermined. In other embodiments, a limit value for the difference between two relative reflectances of second light sources (e.g. an analysis light source and a monitoring light source). In this case, the relative reflectance is the ratio of the light intensity that is scattered and/or reflected (in particular diffusely reflected) at the analysis region of the test element and detected by the detector when monitoring whether the analysis region is positioned in the test element receptacle in the analysis position to the light scattered and/or (diffusely) reflected by the analysis region of a test element positioned in the analysis position without a sample (blank value). The blank value is preferably determined at the start of a measurement prior to the application of a sample (blank value measurement). If the test element is already misaligned in the Z direction in the case of the blank value measurement, this incorrect positioning can also be identified by means of the method according to the invention (e.g. in the analysis system according to the invention).

In accordance with other embodiments of the present invention, an analysis of a sample on a test element positioned in the test element receptacle in the analysis position is carried out once the monitoring of the correct position of the test element determines that the test element is in the analysis position. In typical embodiments, analyzing the sample comprises the steps of irradiating the analysis region with light from at least one analysis light source; using a detector, detecting responsive analysis signals comprising light scattered and/or reflected at the analysis region; and evaluating the analysis signals by the evaluation unit for obtaining analysis results.

This analysis is carried out by the analysis unit of the analysis system according to the invention. This involves a photometric analysis, which is based on the fact that the light intensity of light scattered and/or reflected (in particular scattered and/or diffusely reflected) at the analysis region experiences, as a result of the reaction of an analyte in the sample with a reagent contained in the analysis region, a measurable change depending on the concentration of the analyte in the sample. In this case, the analysis light source used for analyzing the sample may be one and the same as the monitoring light source that is used for monitoring the positioning of the test element. However, an additional light source may also be present, which is used for analyzing the sample. The analysis signals result from radiation that is scattered and/or (diffusely) reflected at the analysis region and passes through the light-transmissive region of the delimiting element to the detector if the test element is positioned in the test element receptacle of the analysis system in the correct analysis position.

Typically, the same detector is used for monitoring whether the analysis region of the test element is positioned in the analysis position and for analyzing the sample.

In accordance with one embodiment of the present invention, the overall method for analyzing a sample with analysis position monitoring comprises the steps of monitoring whether the analysis region of the test element is positioned in the analysis position; contacting the sample with the analysis region for obtaining a photometrically detectable change in the analysis region; activating a first analysis light source of the analysis unit for irradiating a first zone of the analysis region and detecting first analysis signals comprising light scattered and/or reflected by the first zone; activating a second analysis light source of the analysis unit for irradiating a second zone of the analysis region, said second zone being arranged in a manner offset relative to the first zone, and detecting second analysis signals comprising light scattered and/or reflected by the second zone; comparing the first and second analysis signals by the evaluation unit for obtaining comparison results and selecting the first or the second analysis signals on the basis of the comparison results; and determining an analyte concentration contained in the sample by evaluation of the selected first or second analysis signals.

In other embodiments, this overall method may further comprise the initial step of introducing a test element into the test element receptacle, which can be carried out manually or automatically.

The order of the steps is not fixed at this order in this method; that is, these steps can be carried out in any suitable and sufficient order for the overall analysis as desired. For example, the monitoring step can also take place at a later point in time. Furthermore, the monitoring step can also be carried out a number of times. Similarly, the contacting the sample step can take place before the introducing step or even before the monitoring step.

The two zones of the analysis region that are irradiated by the two analysis light sources can be arranged such that they partly overlap or are separate from one another in the analysis region. By way of example, zones of the analysis region that lie alongside one another in the Y direction are illuminated by the two analysis light sources. The method carried out with the aid of the two analysis light sources serves to select that zone in the analysis region which is better suited to an evaluation of the analyte concentration in the sample.

By way of example, the analysis signal which was attenuated to a greater extent by the photometrically detectable change in the analysis region is selected for the analysis of the sample. This method is employed in order to ensure that the analysis result is obtained from signals which originate from a zone lying completely on the analysis region. Such a method is described for example in WO 00/19185 A1, which is hereby incorporated by reference herein.

In accordance with yet another embodiment of the present invention, steps are included for detecting underdosing of sample in the analysis region one sample has been applied to the sample application location of the test element. Exemplary steps for detecting underdosing of sample include the steps of applying a sample to the sample application location of the test element; activating at least one analysis light source for irradiating a first partial region of the analysis region and, using a detector, detecting first detection signals comprising the analysis light scattered and/or reflected by the first partial region; activating a monitoring light source for irradiating a second partial region of the analysis region, the second partial region typically being further away from the sample application location than the first partial region, and, using a detector, detecting second detection signals comprising the monitoring light scattered and/or reflected by the second partial region; calculating a difference value by subtracting the second detection signal from the first detection signal, and comparing the difference value with a predetermined first difference value by the evaluation unit for identifying an underdosing of the sample in the case where the predetermined first difference value is exceeded.

The activation steps can, of course, also be carried out in the opposite order. Such a method for identifying an underdosing of the sample is described for example in EP 0 819 943 A2, which is hereby incorporated by reference herein. The first and second partial regions are partial regions of the analysis region that are separate from one another or at least do not completely overlap.

A sample spreads out after application to the sample application location in the analysis region in such a way that it typically reaches firstly the first partial region of the analysis region and then the second partial region of the analysis region. In the case of an underdosing, the sample may not reach the second partial region of the analysis region at all, or reaches it only partly, such that the calculated difference value exceeds a predetermined first difference value. This is likely due to the scattering capability or reflectivity from the second partial region not being reduced by the sample to the extent that is the case in the first partial region. If an excessively small quantity of the sample is applied to a test element, this can lead to a great corruption of the analysis result because the evaluation always assumes that the analysis region is sufficiently covered with a specific amount of sample.

In yet other embodiments of the present invention, the method for monitoring the correct positioning of a test element in the analysis region in the Z direction can include additional steps for ensuring the accuracy of such monitoring. Exemplary embodiments of a more accurate monitoring method comprise the steps of applying a sample to a sample application location of the test element; activating at least one analysis light source for irradiating a first partial region of the analysis region and, using a detector, detecting first detection signals comprising the analysis light scattered and/or reflected by the first partial region; activating a monitoring light source for irradiating a second partial region of the analysis region, the second partial region typically being further away from the sample application location than the first partial region, and, using a detector, detecting second detection signals comprising the monitoring light scattered and/or reflected by the second partial region; calculating a difference value by subtracting the first detection signals from the second detection signals, and comparing the difference value with a predetermined second difference value for identifying an incorrect position of the analysis region in the Z direction in the test element receptacle.

The activation steps can also be carried out in the opposite order. In this method, which can be effected alone or in combination with the underdosing monitoring described above, the first and the second detection signals are compared by the evaluation unit for identifying an incorrect position of the analysis region in the Z direction in the test element receptacle. Such an incorrect position is identified in the case when the predetermined second difference value is undershot. In such embodiments, the delimiting element is positioned in such a way that light from the monitoring light source that is scattered and/or reflected at the first or second partial region of the analysis region of a test element arranged in an incorrect position in the Z direction generally impinges on the light-opaque region of the delimiting element and the light from the analysis light source that is scattered and/or reflected at the second or first partial region of the analysis region of a test strip arranged in the incorrect position in the Z direction essentially impinges on the light-transmissive region of the delimiting element. As a result, in the case of an incorrect positioning of the analysis region of the test element in the Z direction, the light from the monitoring light source that is scattered and/or reflected is blocked by the light-opaque region in such a way that it generally does not reach the detector. By contrast, despite the incorrect positioning in the Z direction, the light from the analysis light source that is scattered and/or reflected generally impinges on the light-transmissive region of the delimiting element and thus passes through the light-transmissive region towards the detector.

It follows from this that the second detection signal decreases, while the first detection signal remains virtually unchanged as a result of the incorrect positioning, such that the predetermined second difference value is undershot by the calculated difference value, from which the incorrect position of the analysis region in the Z direction can be identified. The advantage of this method is that the analysis and monitoring light sources that are already present for the underdosing identification, if appropriate, and the detection signals of the detector that result from the irradiation of the two partial regions by means of said light sources can be used not only for an underdosing monitoring but also for the monitoring of the position of the analysis region in the Z direction. Therefore, it is merely necessary to correspondingly program a comparison unit of the evaluation unit, such that a comparison of the calculated difference value with the predetermined second difference value is effected (in addition or as an alternative to the comparison of the calculated difference value with the predetermined first difference value).

In some embodiments of the present invention, the at least one analysis light source and the monitoring light source may be preferably activated sequentially. In other embodiments, the monitoring light source can further be used for identifying the presence of a sample in the analysis region, for triggering activation of the monitoring light source for irradiating the second partial region, and subsequently detecting the change in the light scattered and/or reflected by the second region (by comparison with the blank value). As soon as the presence of the sample has been identified in this way in the analysis region, various measurements, for example monitoring the correct positioning of the test element, for analyzing the sample and/or for underdosing monitoring can be initiated automatically in the analysis system used.

Embodiments of the method of the present invention the method typically comprise one or more of the following steps:
1. Measuring blank value (detecting the responsive signals— light scattered and/or reflected at the analysis region— from a first analysis light source, a second analysis light source and/or a monitoring light source, no sample being present on the test element).
2. Wetting identification (detecting a change in the light from a monitoring light source that is scattered and/or reflected by the analysis region, for identifying the presence of a sample).
3. Waiting time, (waiting while a specific time period elapses in order to ensure a distribution of the sample in the analysis region after the presence of a sample has been identified).
4. Measuring kinetics (detecting the responsive signals— light scattered and/or reflected by the analysis region— from the first analysis light source and/or the second analysis light source during the reaction of an analyte from the sample with reagents contained in the analysis region).
5. As appropriate, selecting the analysis signals from one of the first or second analysis light sources (the analysis signals which result from the responsive signals from the selected analysis light source that is scattered and/or reflected at the analysis region are used for the analysis of the sample, such as for determining an analyte concentration contained in the sample).
6. Monitoring underdosing (comparing the first and second detection signals which result from the scattered and/or reflected light from the analysis light source and the monitoring light source, respectively, an underdosing of the sample being identified when a predetermined first difference value is exceeded by a calculated difference value).
7. Monitoring of the positioning of the analysis region of the test element in the Z direction in the test element receptacle (comparing the first and second detection signals which result from the scattered and/or reflected light from the analysis light source and the monitoring light source, respectively, with a second difference value for identifying an incorrect position of the analysis region in the Z direction if the predetermined second difference value is undershot).

The order of the seven described steps of this method can be varied in as suitable and as desired in the particular embodiments. By way of example, Step 7 can be carried out after any of Steps 1, 2, 3, 4, 5, 6, or after a plurality of said steps.

The kinetics measurement of Step 4 is typically used in order to be able to identify when a reaction of the analyte contained in the sample with the reagents contained in the analysis region has concluded or should conclude. For example, reaching a steady state with respect to the responsive signals being detected by the detector may be used to define an analysis termination criterion.

The invention furthermore relates to an analysis system comprising an analysis light source for irradiating a first partial region of the analysis region of a test element in the test element receptacle, a monitoring light source for irradiating a second partial region of the analysis region of the test element, the second partial region typically being further away from a sample application location of the test element than the first partial region, and at least one detector for detecting the responsive signals—light scattered and/or reflected by the analysis region—from the analysis light source and the monitoring light source for obtaining a first detection signal and a second detection signal, respectively, a delimiting element being positioned in the system in such a way that responsive signals from the monitoring light source that is light scattered and/or reflected at the second partial region of an analysis region arranged in an incorrect position in the Z direction generally impinges on the light-opaque region of the delimiting element, and the responsive signals from the analysis light source that is scattered and/or reflected at the first partial region of an analysis region arranged in the incorrect position in the Z direction generally impinges on the light-transmissive region of the delimiting element, the evaluation unit containing a comparison unit which identifies an incorrect position of the analysis region in the Z direction in the test element receptacle in the event that a predetermined difference value is undershot compared to a difference valued calculated from subtracting the first from the second detection signal. A corresponding arrangement of the delimiting element will be achieved by configuring the boundary between the light-transmissive region and the light-opaque region according to the spacing of the illuminated partial regions of the analysis region and with the maximum possible incorrect positioning in the Z direction.

In yet other embodiments, if an incorrect positioning of the analysis region of a test element in the Z direction in the test element receptacle is identified by means of the embodiments of the method or the analysis system according to the present invention, then the analysis system can be configured to output an optical, acoustic or haptic error message, such that a user can rectify the incorrect positioning.

The present invention is explained in further detail with reference to the drawings of one or more embodiments thereof.

FIG. 1 shows a strip-type test element that can be used for the embodiments of the method or the analysis system according to the present invention. The test element 1 comprises an analysis region 2 for the analysis of a sample. In one embodiment, a test element 1 may further comprise a recess 3, with which a pin of an analysis system can engage in order to position and fix the test element 1 in the X direction and Y direction in the test element receptacle of the analysis system.

A first zone 4 is depicted in the analysis region 2 of the test element 1, said first zone being illuminated by a first analysis light source (LED 1A). A second zone 5 is furthermore marked in the analysis region, said second zone being irradiated with the light from a second analysis light source (LED 1B). The first zone 4 and the second zone 5 are arranged alongside one another in the Y direction of the test element 1. The first zone 4 or the second zone 5 represent a first partial region 6 of the analysis region. Furthermore, a second partial region 7 of the analysis region 2 is illuminated by a monitoring light source (LED 2). In one embodiment, the second partial region 7 is further away from a sample application location 8 than the first partial region 6. After a sample has been applied to the sample application location 8, it is transported towards the analysis region 2, typically by a capillary gap (not illustrated). As illustrated, the sample therefore first reaches the first partial region 6 of the analysis region, which is formed by the first zone 4 and the second zone 5. The sample then reaches the second partial region 7, which is irradiated by the monitoring light source. As soon as the sample reaches the second partial region 7, the scattering capability or reflectivity thereof changes, such that when the second partial region 7 is irradiated with light from the monitoring light source, a change in the intensity of the light scattered and/or reflected by the second partial region 7 is detected, such that the presence of the sample in the second partial region 7 and hence in the analysis region 2 can be identified on the basis of the change in the detection signal.

In order to identify an incorrect positioning of the analysis region 2 of this test element 1 in the Z direction in the test element receptacle of an analysis system, in one embodiment one of the two analysis light sources is activated for the irradiation of the first zone 4 or the second zone 5 in the first partial region 6 of the analysis region 2, and the responsive signal—light scattered and/or reflected by the analysis region 2—is detected by means of a detector in order to obtain a first detection signal. A monitoring light source is then activated for the irradiation of the second partial region 7 of the analysis region 2 and the responsive signal—light scattered and/or reflected by the analysis region 2—is detected by means of a detector for obtaining a second detection signal. In other embodiments, the system may use a single detector for detecting all such signals. The first and the second detection signals are subsequently compared. A difference value is calculated by subtracting the first detection signal from the second detection signal, or vice versa. This is done in an evaluation unit of the analysis system. In the event that the calculated difference value fails to meet and/or exceed a predetermined second difference value, an incorrect position of the analysis region 2 in the Z direction (generally perpendicular to the major plane of the test element 1) is identified.

The difference value typically occurs as a result of delimiting element being positioned in such a way that light from the monitoring light source that is scattered and/or reflected at an analysis region arranged in an incorrect position in the Z direction generally impinges on the light-opaque region of the delimiting element and the light from the analysis light source that is scattered and/or reflected at an analysis region 2 arranged in the incorrect position in the Z direction generally impinges on the light-transmissive region of the delimiting element. Therefore, the light from the monitoring light source that is scattered and/or reflected in the second partial region 7 is blocked from the detector by the light-opaque region of the delimiting element and the light from the analysis light source that is scattered and/or reflected in the first partial region 6 is scattered and/or (preferably diffusely) reflected onto the detector through the light-transmissive region of the delimiting element. This results in a greatly reduced second detection signal and a largely constant first detection signal, such that the calculated difference value undershoots the predetermined second difference value. Consequently, the incorrect position of the analysis region 2 of the test element 1 in the Z direction is identified by this comparison.

In the event that a predetermined first difference value is exceeded by the calculated difference value, by contrast, an underdosing of the sample can be identified because the second detection signal turns out to be higher than the first detection signal. When the predetermined first difference value is generally met by the calculated difference value, this typically indicates not only proper positioning but also sufficient dosing.

Figure 2A:
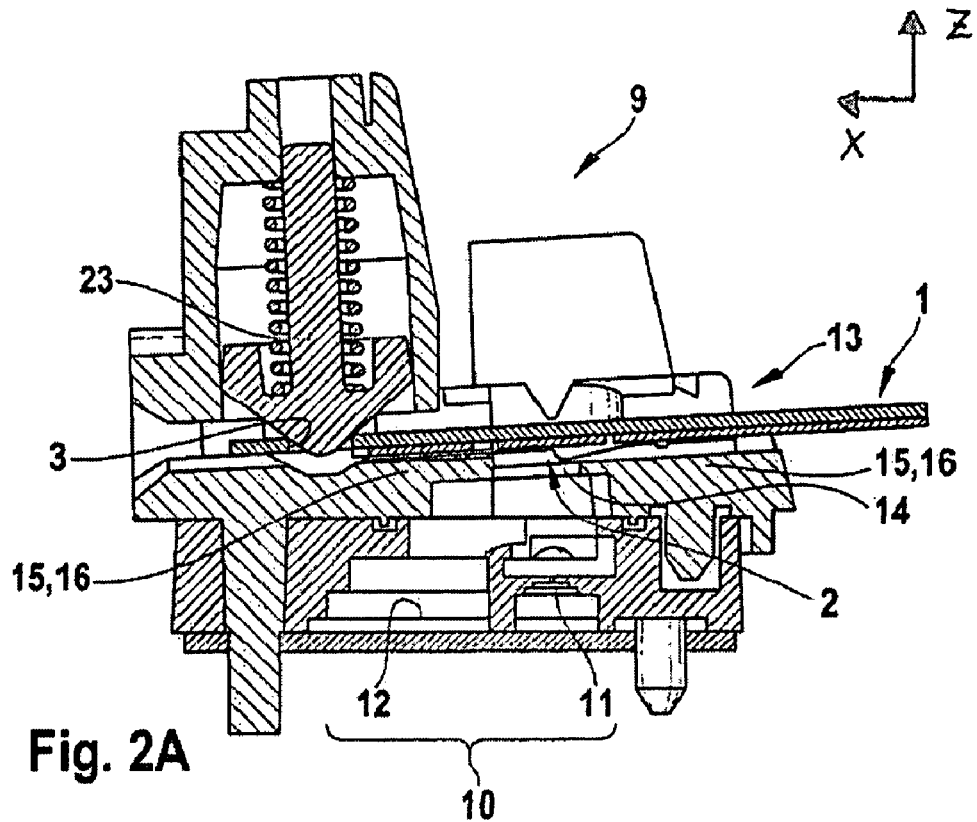
FIG. 2A illustrates a cross sectional view of an analysis system according to embodiments of the present invention with an analysis region of a test element that is positioned in the analysis position.

FIG. 2A shows an embodiment of an analysis system according to the present invention with an analysis region of a test element that is positioned in the analysis position.

As shown, the analysis system 9 comprises an analysis unit 10 comprising a light source 11 and a detector 12. A test element 1 is inserted into a test element receptacle 13, said test element being positioned and fixed in the X direction and Y direction by a pin 23, which engages into a recess 3 in the test element 1. In FIG. 2A, the test element 1 is situated in the analysis position. As shown, the test element 1, and in particular its analysis region 2, is positioned correctly relative to the analysis unit 10 in the Z direction. The light from the light source 11 passes through a light-transmissive region 14 of a delimiting element 15 to the analysis region 2 of the test element 1. In one embodiment, the light-transmissive region 14 comprises a window framed by a light-opaque region 16 of the delimiting element 15. The light from the light source 11 is scattered and/or reflected at the analysis region 2 of the test element 1 and once again passes through the light-transmissive region 14 of the delimiting element 15 and at least one portion of the scattered and/or (preferably diffusely) reflected light then impinges on the detector 12 for generating a detection signal.

Figure 2B:
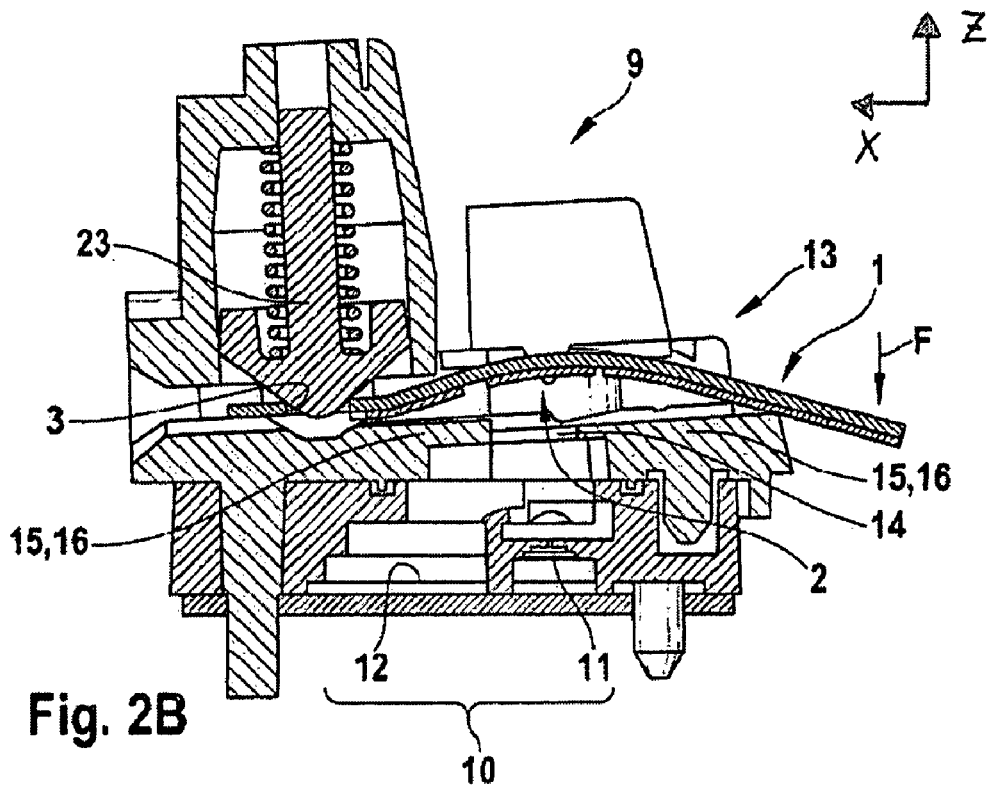
FIG. 2B illustrates a cross sectional view of the analysis system according to the present invention and in accordance with FIG. 2A, with an analysis region of a flexed test element that is incorrectly positioned in the Z direction.

The embodiment of the analysis system illustrated in FIG. 2B comprises generally the same component parts as the analysis system illustrated in FIG. 2A, which are designated by the same reference symbols.

Referring now to FIG. 2B, in the event that the test element 1 is flexed on account of a force action F, the result is an incorrect positioning of the analysis region 2 in the Z direction, which is normal to the spatial plane comprising the X and Y directions. As a result, the light that is emitted by the light source 11 and passes through the light-transmissive region 14 of the delimiting element 15 is scattered and/or (preferably diffusely) reflected at the analysis region 2, but if the light irradiates, for example, the second partial region of the analysis region then the scattered and/or reflected light typically is no longer able to reach the detector 12 on account of the light-opaque region 16 of the delimiting element 15. A comparison of the detection signals obtained by the detector 12 therefore reveals that a limit value is undershot, such that the incorrect positioning of the analysis region 2 in the Z direction can be identified.

Figure 3:
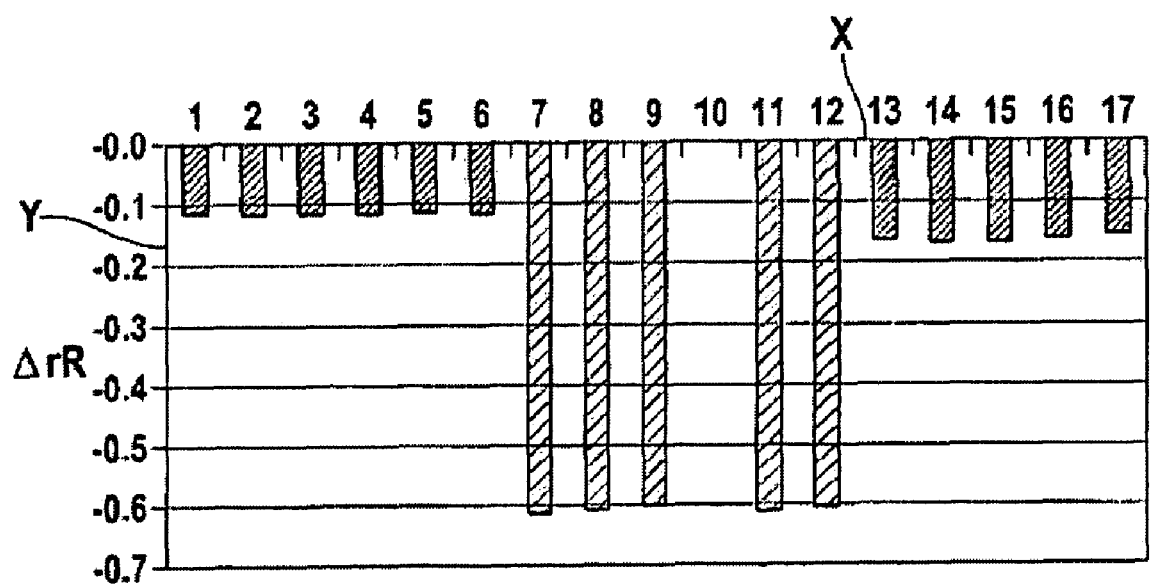
FIG. 3 shows a graph representing exemplary difference values of the relative reflectance of the light from an analysis light source and a monitoring light source.

FIG. 3 shows a graph representing difference values calculated by subtracting the first detection signal from the second detection signal. The second detection signal comprises the signal detected from irradiating the second partial region of the analysis region by means of a monitoring light source, and the first detection signal comprises the signal detected from irradiating the first partial region of the analysis region by means of an analysis light source.

In this case, the difference between the relative reflectances is plotted on the Y axis, and the number of the measurement is plotted on the X axis. Measurements without a sample (blank value measurements), with a bent test strip, and measurements with a sample are represented. The measurements 1 to 6 show the difference between the relative reflectances [$\Delta rR = rR(LED\ 2) - rR(LED\ 1) = rR(\text{monitoring light, source}) - rR(\text{analysis light source})$] which were measured in the case of a test element positioned correctly in the analysis position without a sample (blank value measurements). It can be discerned in this case that the relative reflectance of the LED 2 is somewhat smaller than the relative reflectance of the LED 1, thus resulting in a difference between the relative reflectances of approximately −0.12. This difference likely results, inter alia, from the different optical paths and from the different wavelengths of the light from the two light sources.

In the case where the test strip is bent (measurements 7 to 9 and 11 to 12), the relative reflectance of the LED 2 is greatly reduced since its radiation scattered and/or reflected at the analysis region of the test element is blocked towards the detector by the delimiting element. By contrast, the relative reflectance of the LED 1 is hardly influenced by the bending of the test strip. Therefore, the difference between the relative reflectances decreases greatly to approximately −0.6. An incorrect positioning of the analysis region of this test element in the Z direction can therefore be identified if this difference between the relative reflectances is compared with a difference value of −0.3, for example, which is undershot by this measured difference signal.

In the case of measurement 10 of FIG. 3, the test strip was bent to such a great extent that it left the mechanical fixing by the pin in the analysis system and the analysis system identified a fault by virtue of an associated opening of an optical switch and, therefore, no measurement took place.

In measurements 13 to 17 of FIG. 3, the analysis region of the test element contained a sample that influenced the difference between the relative reflectances depending on the concentration of an analyte contained therein. On account of the concentration dependence, the difference between the relative reflectances is now approximately −0.17. These difference values still differ clearly, however, from the difference values that are reduced from a bending of the test strip.

Figure 4:
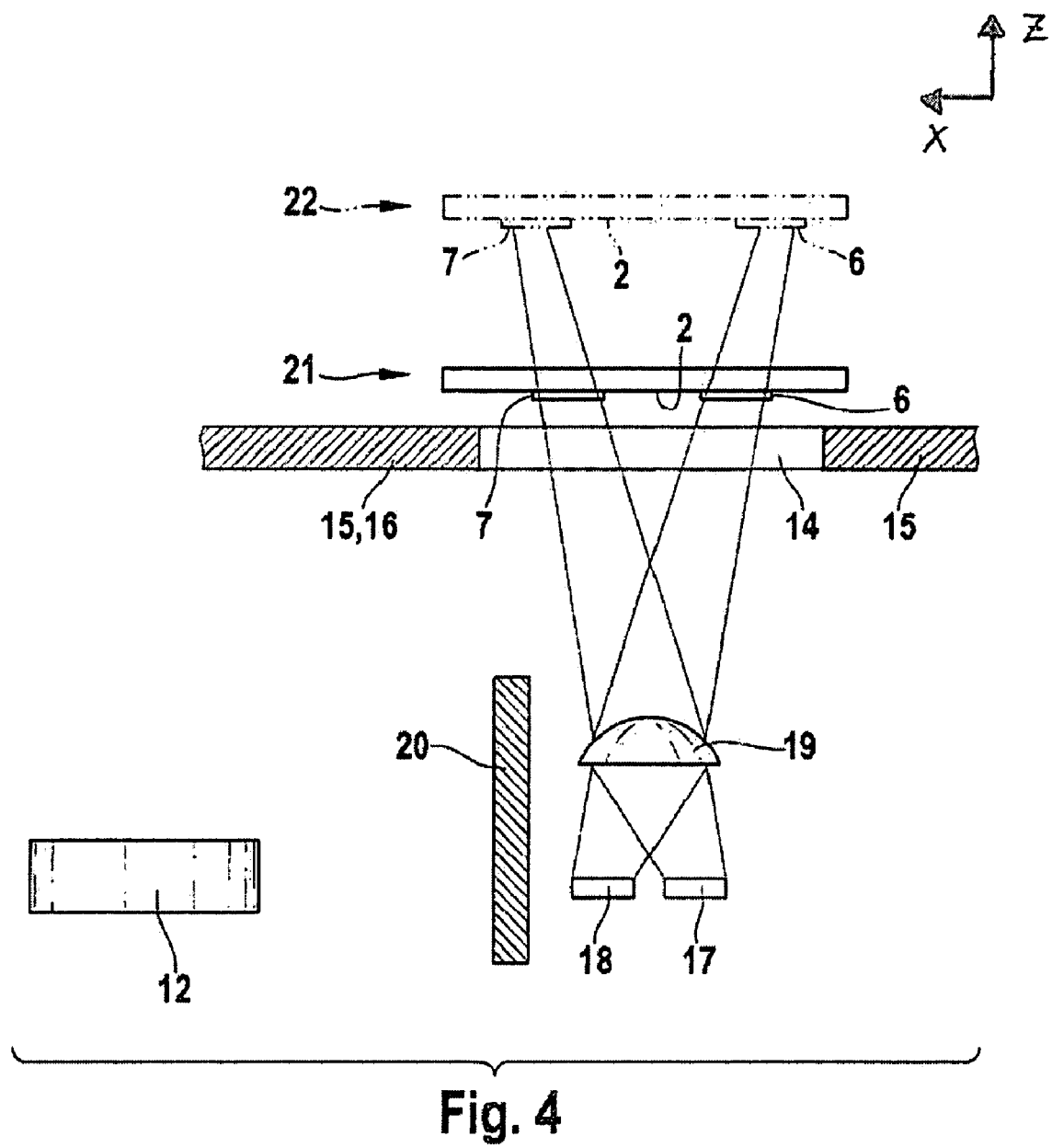
FIG. 4 illustrates a side schematic view of the arrangement of a delimiting element in the method according to the invention and the analysis system according to embodiments of the present invention.

FIG. 4 schematically shows the arrangement of a delimiting element in one embodiment of an analysis system according to the present invention.

Referring now to FIG. 4, the analysis system comprises a monitoring light source 17 and an analysis light source 18, the light from which impinges on the analysis region 2 of a test element 1 through a lens 19 and through the light-transmissive region 14 of a delimiting element 15. A diaphragm 20 may be arranged between a detector 12 and the general location of the two light sources 17, 18 in order to prevent light from being radiated indirectly from the light sources 17, 18 onto the detector 12. In the case of an analysis region 21 positioned correctly in the test element receptacle of an analysis system, the light from the analysis light source 18 impinges on a first partial region 6 of the analysis region 2, is scattered and/or (diffusely) reflected there and partly reaches the detector 12. The light from the monitoring light source 17 impinges on a second partial region 7 of the analysis region 2, is scattered of (diffusely) reflected there and likewise impinges partly on the detector 12. The difference between the resultant detection signals therefore lies above a predetermined second difference value. In the case of a test element having an analysis region in an incorrect position 22 in the Z direction, the light from the analysis light source 18 impinges on a first partial region 6, is scattered and/or (diffusely) reflected there and passes partly to the detector 12. The light from the monitoring light source 17 impinges on a second partial region 7 of the analysis region in incorrect position 22, is scattered and/or (diffusely) reflected there but does not pass to the detector 12 because the light-opaque region 16 of the delimiting element 15 effectively prevents this. The difference between the two detection signals therefore lies below a predetermined second difference value, such that an incorrect positioning of the analysis region 22 is identified.

The features disclosed in the above description, the claims and the drawing may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

LIST OF REFERENCE SYMBOLS

1 Test element
2 Analysis region
3 Recess
4 First zone
5 Second zone
6 First partial region
7 Second partial region
8 Sample application location
9 Analysis system
10 Analysis unit/monitoring unit
11 Light source
12 Detector
13 Test element receptacle
14 Light-transmissive region
15 Delimiting element
16 Light-opaque region
17 Monitoring light source
18 Analysis light source
19 Lens 20 Diaphragm
21 Correctly positioned analysis region
22 Analysis region in incorrect position
23 Pin

The invention claimed is:

1. A method for monitoring whether an analysis region of a test element holding a sample is positioned in an analysis position for analyzing the sample using an analysis system, the analysis system having a test element receptacle and an analysis unit, the analysis position being relative to the analysis unit as the test element is mounted in the test element receptacle, the method comprising the steps of:
   irradiating the analysis region with light from at least one monitoring light source;
   detecting responsive detection signals by a detector, the detection signals comprising light scattered and/or reflected at the analysis region;
   delimiting a light-transmissive region arranged between the test element and the detector by a delimiting element comprising a light-opaque region and positioned relative to the monitoring light source and the detector such that detection signals generally impinge upon the light-opaque region and not the detector when the test element is mounted in the test element receptacle in an incorrect position in a Z direction;
   evaluating the detection signals using an evaluation unit; and
   comparing the detection signals with at least one predetermined limit value corresponding to a correct analysis position with respect to the Z direction.

2. The method according to claim 1, wherein the predetermined limit value corresponds to a relative reflectance of light scattered and/or diffusely reflected at the analysis region of the test element for an analysis region in a correct position in a Z direction.

3. The method according to claim 1, further comprising the step of analyzing the sample when it is determined that the test element is in a correct analysis position, said analyzing comprising the steps of:
   irradiating the analysis region with light from at least one analysis light source;
   using the detector, detecting responsive analysis signals comprising light scattered and/or reflected at the analysis region; and
   evaluating the analysis signals by the evaluation unit for obtaining analysis results.

4. The method according to claim 3, wherein the detector comprises at least first and second detectors, the first detector configured for detecting the detection signals, the second detector configured for detecting the analysis signals.

5. The method according to claim 3, wherein the at least one analysis light source comprises at least first and second analysis light sources, the analysis region comprises at least first and second zones, the irradiating step comprises irradiating the first zone with the first analysis light source and irradiating the second zone with the second analysis light source, the detecting step comprises detecting first analysis signals comprising light scattered and/or reflected at the first zone and detecting second analysis signals comprising light scattered and/or reflected at the second zone, and the evaluation step comprising comparing the first and second analysis signals using the evaluation unit in order to select one of the first and second analysis signals for purposes of determining an analyte concentration contained in the sample.

6. The method according to claim 1, further comprising the step of detecting underdosing of the sample in the analysis region once the sample has been applied to a sample application location of the test element, the detecting comprising the steps of:
   applying the sample to the sample application location of the test element;
   activating at least one analysis light source for irradiating a first partial region of the analysis region and, using a detector,
   detecting first detection signals comprising the analysis light scattered and/or reflected by the first partial region;
   activating the at least one monitoring light source for irradiating a second partial region of the analysis region, the second partial region typically being further away from the sample application location than the first partial region, and, using a detector, detecting second detection signals comprising the monitoring light scattered and/or reflected by the second partial region; and
   calculating a difference value by subtracting the second detection signal from the first detection signal and comparing the difference value with a predetermined first difference value by the evaluation unit for identifying an underdosing of the sample in the case where the predetermined first difference value is exceeded.

7. The method according to claim 6, wherein the at least one analysis light source and the at least one monitoring light source are activated sequentially.

8. The method according to claim 1, wherein the analysis region comprises first and second partial regions, the second partial region being further away from a sample application location than the first partial region, and wherein the irradiating step comprises irradiating the second partial region by the at least one monitoring light source, the detection signals comprising light scattered and/or reflected at the second partial region, and further comprising the steps of:
   irradiating the first partial region of the analysis region by at least one analysis light source;
   using the detector, detecting first detection signals comprising the analysis light scattered and/or reflected by the first partial region;
   calculating a difference value by subtracting the first detection signals from the second detection signals; and
   comparing the difference value with a predetermined second difference value for identifying an incorrect position of the analysis region in the Z direction in the test element receptacle.

9. The method according to claim 8, wherein the at least one analysis light source and the at least one monitoring light source are activated sequentially.

10. The method according to claim 1, wherein the test element comprises a sample application location, and further comprising the steps of applying the sample to the sample application location, irradiating a partial region of the analysis region, and detecting a comparable change in the responsive detection signals comprising light scattered and/or reflected by the partial region in order to identify the presence of the sample in the analysis region.

11. An analysis system for analyzing a sample, the system comprising an analysis unit and a test element having an analysis region for holding the sample, the analysis unit comprising a test element receptacle configured for positioning the analysis region of the test element in an analysis position relative to the analysis unit, the analysis system further comprising
   a monitoring unit for monitoring whether the analysis region of the test element is positioned in the test element receptacle in the analysis position, the monitoring unit comprising at least one monitoring light source configured for irradiating the analysis region with light, and a detector configured for detecting monitoring detection signals comprising responsive light scattered and/or reflected at the analysis region;

a delimiting element arranged between the detector and the test element mounted in the test element receptacle, said delimiting element having a light-opaque region and being positioned relative to the monitoring light source and the detector in such a way that the monitoring detection signals from a test element is arranged in the test element receptacle in an incorrect position in the Z direction generally impinges on the light-opaque region and not the detector; and an evaluation unit configured for comparing the monitoring detection signals with at least one predetermined limit value for identifying an incorrect position of the analysis region in the Z direction in the case where the limit value is undershot.

12. The analysis system according to claim 11, wherein the analysis region comprises first and second partial regions, the at least one monitoring light source being configured for irradiating the second partial region, and wherein the analysis system further comprises an analysis light source configured for irradiating the first partial region, the detector being configured for detecting first detection signals comprising responsive light scattered and/or reflected by the first partial region, and for detecting second detection signals comprising responsive light scattered and/or reflected by the second partial region, the delimiting element being positioned so that light from the monitoring light source that is scattered and/or reflected at the second partial region generally impinges on the light-opaque region when the analysis region is in an incorrect position in the Z direction and the light from the analysis light source that is scattered and/or reflected at the first partial region generally impinges on the light-transmissive region when the analysis region is in the incorrect position in the Z direction, the evaluation unit being configured to calculate a difference value by subtracting the first detection signal from the second detections signal, the evaluation unit further being configured to compare the calculated difference valued with a predetermined difference value and identify an incorrect position of the analysis region in the Z direction in the test element receptacle when the predetermined difference value is undershot.

* * * * *